US00PP30008P3

(12) United States Plant Patent
Grard et al.

(10) Patent No.: US PP30,008 P3
(45) Date of Patent: Dec. 25, 2018

(54) APPLE TREE NAMED 'GRADISCA'

(50) Latin Name: ***Malus domestica* Borkh.**
Varietal Denomination: Gradisca

(71) Applicants: Olivier Grard, Mudaison (FR); Alexandre Grard, Mudaison (FR)

(72) Inventors: Olivier Grard, Mudaison (FR); Alexandre Grard, Mudaison (FR)

( * ) Notice: Subject to any disclaimer, the term of this patent is extended or adjusted under 35 U.S.C. 154(b) by 64 days.

(21) Appl. No.: 15/530,344

(22) Filed: Dec. 27, 2016

(65) Prior Publication Data

US 2018/0184556 P1 Jun. 28, 2018

(51) Int. Cl.
*A01H 5/08* (2018.01)
*A01H 6/74* (2018.01)

(52) U.S. Cl.
USPC ..... Plt./161

CPC ..... *A01H 6/7418* (2018.05); *A01H 5/08* (2013.01)

(58) Field of Classification Search
USPC ..... Plt./156, 161, 168
See application file for complete search history.

(56) References Cited

PUBLICATIONS

UPOV-PLUTO: Plant Variety Database, Apr. 11, 2018, citation for 'Gradisca'. 1 page.*

* cited by examiner

*Primary Examiner* — Susan McCormick Ewoldt
*Assistant Examiner* — Karen M Redden
(74) *Attorney, Agent, or Firm* — Michelle Bos Legal LLC

(57) ABSTRACT

'Gradisca' apple tree is the product of an open pollination of 'Fuji' apple, and is characterized by its bright red fruit and good production capacity. Fruit of 'Gradisca' is sweet and perfumed, and colors well in hot weather. 'Gradisca' is distinguished from its parent 'Fuji' by its more perfumed fruit and more intense red overcolor.

5 Drawing Sheets

Latin name: *Malus domestica* Borkh.
Variety denomination: 'Gradisca'.

BACKGROUND OF THE VARIETY

'Gradisca' is a new and distinct cultivar of apple tree *Malus domestica* Borkh discovered in an established 'Fuji' (not patented) orchard. This new cultivar originated as a seedling resulting from the open pollination of a 'Fuji' apple tree, and is characterized by its bright red fruit and good production capacity. 'Gradisca' was first observed in Mudaison, France in 1994. Asexual reproduction by budding and grafting was first carried out at Mudaison in 1996. 'Gradisca' has since been observed to remain true to type over successive asexually propagated generations.

BRIEF DESCRIPTION OF THE VARIETY

'Gradisca' was first selected for its attractive bright red fruit and for its productivity. Fruit of 'Gradisca' is sweet and perfumed, and colors well in hot weather. There is no equivalent apple with the same organoleptic qualities in the same picking period.

'Gradisca' is distinguished from its parent 'Fuji' by its more perfumed fruit and more intense red overcolor. Fruit of 'Gradisca' is similar in color to that of 'Rosy Glow' (not patented), but 'Gradisca' is easily distinguished from 'Rosy Glow' by its early harvest maturity, at least one month prior to 'Rosy Glow'.

BRIEF DESCRIPTION OF THE PHOTOGRAPHS

Figure 1:
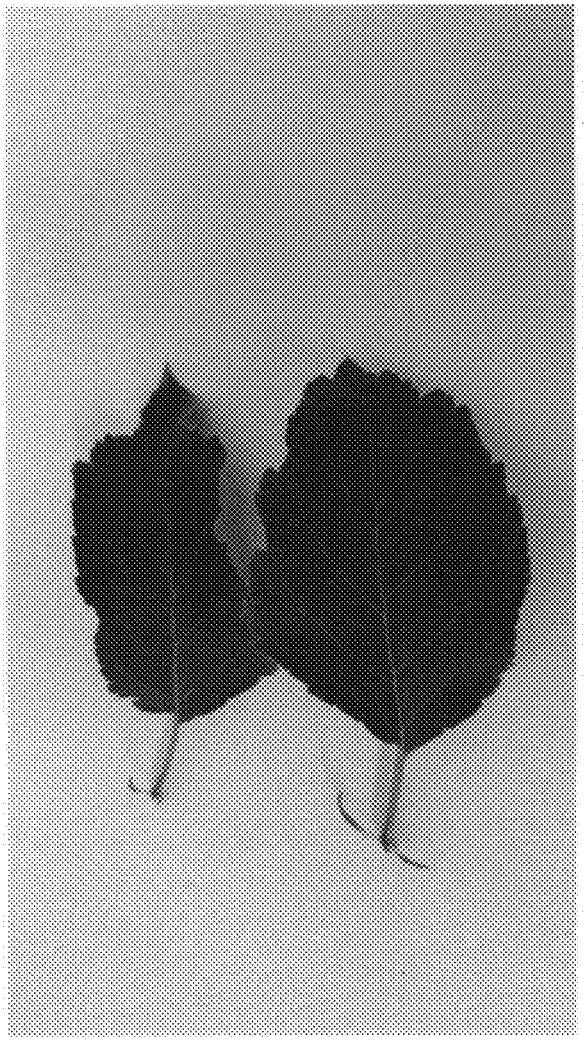
Figure 2:
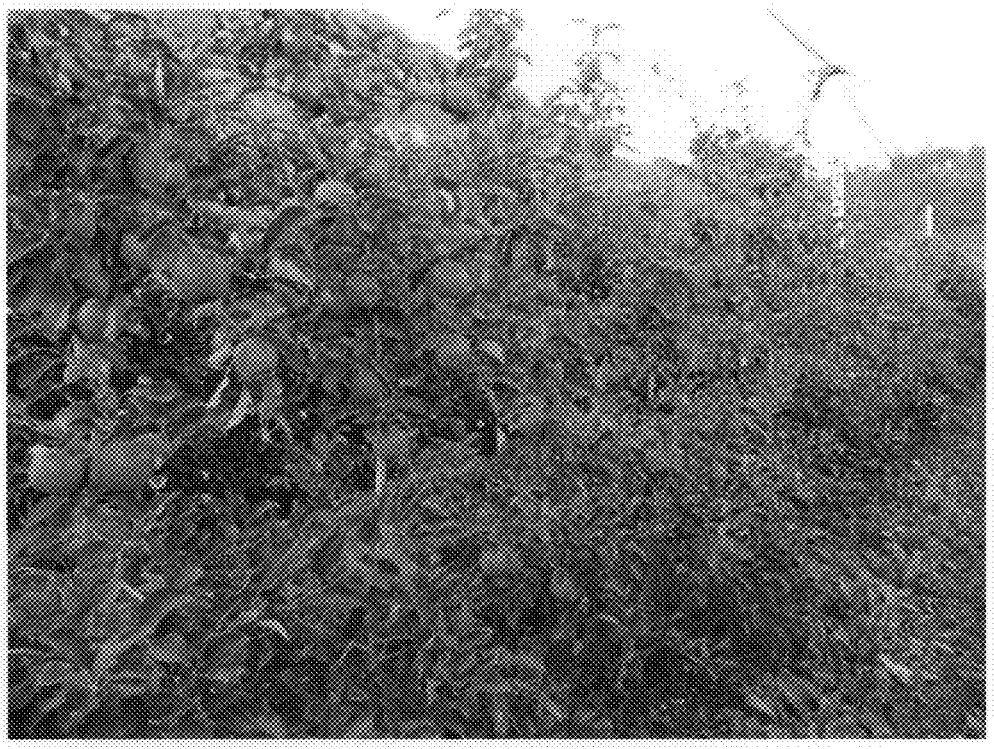
Figure 3:
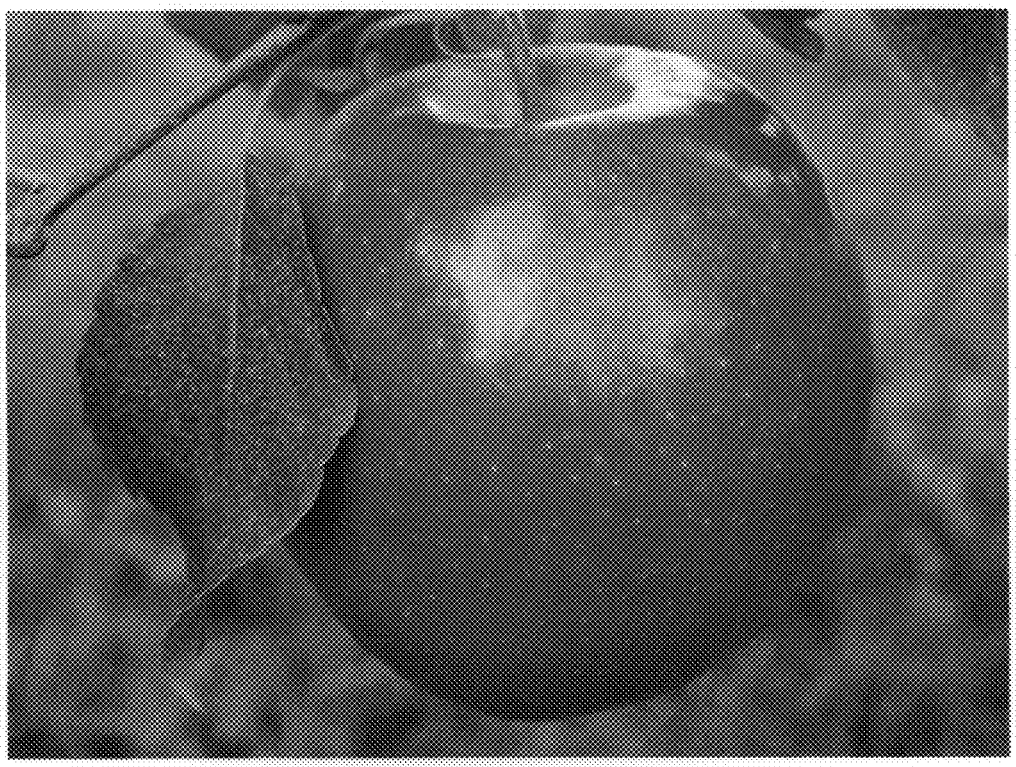
Figure 4:
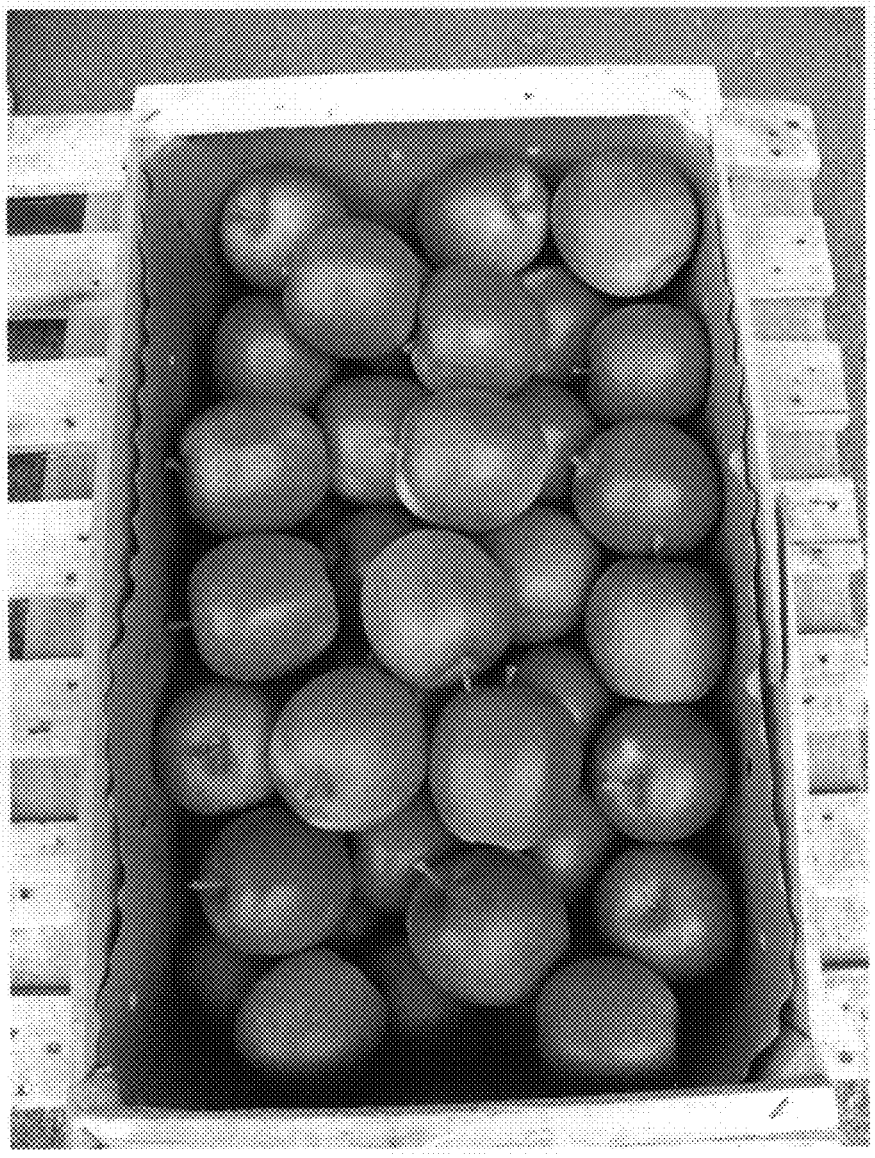
Figure 5:
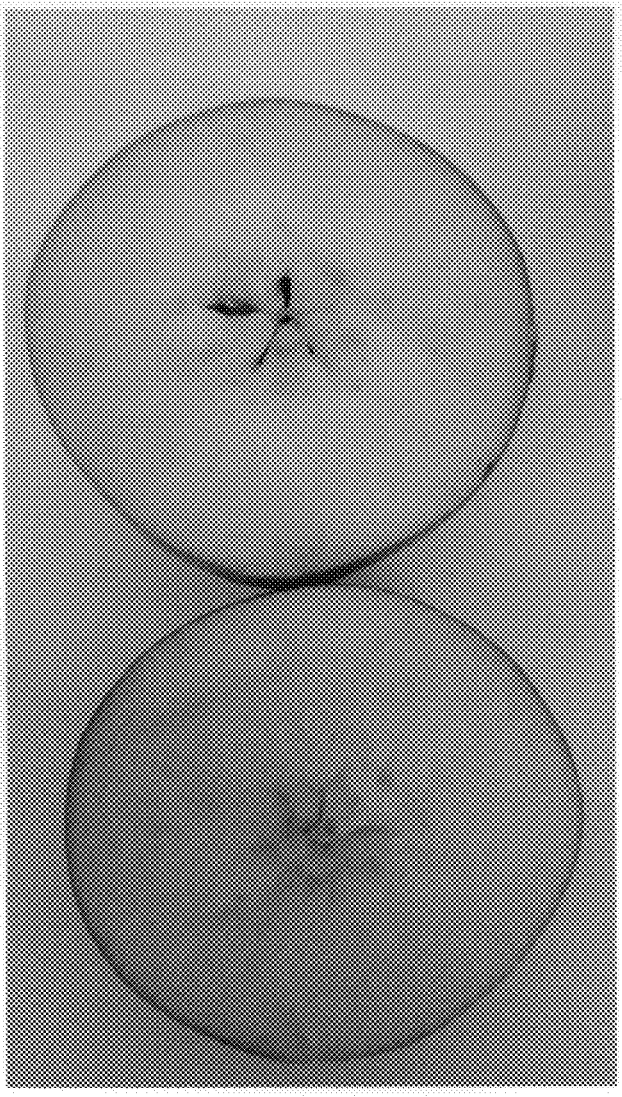

FIG. 1 shows the leaves of 'Gradisca';
FIG. 2 shows 4$^{th}$-leaf trees of 'Gradisca' one week before picking;
FIG. 3 shows a fruit of 'Gradisca';
FIG. 4 shows picked whole fruit of 'Gradisca'; and
FIG. 5 shows a sectioned fruit of 'Gradisca'.

DETAILED BOTANICAL DESCRIPTION OF THE VARIETY

The following detailed botanical description is based on observations made during the 2016 growing season (unless otherwise noted) at Mudaison, France of four-year-old trees grown on 'M9 EMLA' rootstock (not patented). All colors are described according to The Royal Horticultural Society Colour Chart, 5$^{th}$ edition, version 2. It should be understood that the characteristics described will vary somewhat depending upon cultural practices and climatic conditions, and will vary with location and season. Quantified measurements are expressed as an average of measurements taken from a number of individual plants of the new variety. The measurements of any individual plant or any group of plants of the new variety may vary from the stated average.

Tree:

*Vigor.*—Vigorous.
*Type.*—Ramified, drooping.
*Habit.*—Semi-upright tree with one trunk and one leader, main branch spreading.
*Height.*—3.20 m.
*Spread.*—2 m.

*Trunk diameter.*—5.8 cm at 30 cm above the graft union.
*Bark texture.*—Fairly smooth with slight crevice and small lenticels.
*Bark coloration.*—Light brown 162A.
*Lenticels.*—2 mm; light beige 159D.

Branch (fruiting branches located at around 1 m above the graft union):
*Length.*—1.50 m.
*Diameter.*—16 mm to 20 mm.
*Crotch angle.*—80° to 90°.
*Color.*—Dark brown with grey highlights 165B.
*Lenticels.*—1.5 mm; beige 159D; 4 to 8 per $cm^2$.

One-year-old shoot:
*Length.*—25 cm to 35 cm.
*Color.*—Very light brown 160A.
*Pubescence.*—Strong.
*Thickness.*—3 mm to 5 mm.
*Internode length.*—13 mm to 22 mm.
*Lenticels.*—1 mm; white NN155A; 11 per $cm^2$.

Winter hardiness:
*Hardiness.*—Hardy in area tested (USDA hardiness zone 9A).
*Chilling requirement.*—Medium; between 450 hours and 650 hours.

Flower buds:
*Quantity per spur.*—4 to 5.
*Shape.*—Globose.
*Diameter.*—10 mm to 12 mm.
*Color.*—Red purple 63B.

Flowers:
*Color (balloon stage).*—Light pink 36D.
*Diameter of open flower.*—2 cm.
*Depth.*—0.8 cm.
*Number per cluster.*—4.
*Fragrance.*—Light.
*Pollination requirement.*—Pollenizer required.

Petals:
*Quantity per flower.*—5.
*Shape.*—Ovate.
*Length.*—15 mm to 18 mm.
*Width.*—14 mm to 16 mm.
*Color of upper surface.*—White NN155D.
*Color of lower surface.*—White NN155D.
*Texture.*—Smooth.
*Margin.*—Entire.

Pistils:
*Length.*—12 mm to 13 mm.
*Color.*—Yellow-green 145C.

Anthers:
*Quantity.*—16.
*Size.*—2 mm.
*Pollen.*—Present.
*Pollen color.*—Yellow 9B.

Stigma:
*Size.*—1 mm.
*Color.*—Yellow 11C.

Style:
*Size.*—8 mm.
*Color.*—Yellow-green 145C.

Bloom:
*Date of first bloom.—April* $10^{th}$ (Mudaison, Hérault, southern France).
*Date of full bloom.—April* $14^{th}$ (Mudaison, Hérault, southern France).

Pedicel:
*Length.*—16 mm to 19 mm.
*Diameter.*—3 mm.
*Color.*—Greyed-orange N172C.

Sepals:
*Quantity.*—5.
*Color.—Green* 135B.
*Length.*—8 mm to 11 mm.
*Width.*—2 mm to 3 mm.
*Shape.*—Triangular.
*Margin.*—Entire.
*Texture.*—Weakly pubescent.

Leaves:
*Shape.*—Ovate.
*Length (petiole not included).*—7 cm to 9 cm.
*Width.*—5 cm to 6 cm.
*Length/width ratio.*—1.4 to 1.6.
*Blade margin.*—Biserrate.
*Apex.*—Acuminate.
*Base shape.*—Cuneate.
*Color of top surface.*—Green 134A.
*Color of bottom surface.*—Green 140B.
*Texture.*—Upper surface — Smooth.
*Texture.*—Lower surface — Moderately pubescent.
*Venation.*—Pinnate.
*Vein color.*—Yellow green 1B.
*Attitude in relation to shoot.*—Outward.

Petiole:
*Length.*—18 mm.
*Diameter.*—2 mm.
*Color.*—Green 142A.

Fruit:
*Quantity per cluster.*—4.
*Diameter.*—70 mm to 80 mm.
*Height.*—70 mm to 80 mm.
*Weight.*—200 g.
*Ratio of height to width.*—Nearly 1:1.
*General shape in profile.*—Globose slightly conical.
*Position of maximum diameter.*—At middle.
*Ribbing.*—Absent.
*Crowning at calyx end.*—Absent or weak.
*Aperture of eye.*—Closed.
*Size of eye.*—8 mm.
*Length of sepal.*—4 mm to 7 mm.
*Depth of eye basin.*—9 mm to 13 mm.
*Width of eye basin.*—23 mm to 25 mm.
*Length of stalk.*—13 mm to 19 mm.
*Thickness of stalk.*—4 mm.
*Width of stalk cavity.*—17 mm.
*Depth of stalk cavity.*—13 mm.
*Size of lenticels.*—1.5 mm.
*Bloom of skin.*—Absent.
*Greasiness of skin.*—Absent.
*Background colour of skin.*—Yellow 7A.
*Over colour of skin.*—Red-pink N33A.
*Amount of overcolor.*—70% to 90%.
*Intensity of overcolor.*—Very intense.
*Pattern of overcolor.*—Solid flush.
*Skin texture.*—Fine. smooth.
*Flesh texture.*—Firm and light.
*Aroma.*—Good eating quality, sweet and perfumed.
*Juiciness.*—Juicy.
*Brix.*—13.5 to 15.5.
*Flesh color.*—Yellow 4B.
*Stem color.*—Light pink 39D.

*Locule length.*—18 mm to 23 mm.
*Locule width.*—5 mm to 6 mm.
*Number of locules per fruit.*—5.

Seeds:

*Quantity per fruit.*—8 to 10.
*Shape.*—Oval.
*Color.*—Brown 200D.

Harvest:

*Amount of fruit produced per harvest.*—30 kg per tree.
*Harvest date.*—October 1 to October 13 (2017 growing season, Mudaison, Hérault, southern France).
*Storage characteristics.*—6 months in standard cold storage; 9 months in controlled atmosphere storage.
*Market use.*—Fresh.

Diseases/pests:

*Resistance.*—None noted.
*Susceptibility.*—Susceptible to scab (*Venturia* inaequalis).

We claim:

1. A new and distinct apple tree named 'Gradisca' substantially as described and illustrated herein.

* * * * *